United States Patent
Hossein-Zadeh

(10) Patent No.: US 9,541,528 B2
(45) Date of Patent: Jan. 10, 2017

(54) SENSORS USING OPTICAL RF OSCILLATORS

(71) Applicant: Mani Hossein-Zadeh, Albuquerque, NM (US)

(72) Inventor: Mani Hossein-Zadeh, Albuquerque, NM (US)

(73) Assignee: STC.UNM, Albuquerque, NM (US)

( * ) Notice: Subject to any disclaimer, the term of this patent is extended or adjusted under 35 U.S.C. 154(b) by 39 days.

(21) Appl. No.: 14/213,858

(22) Filed: Mar. 14, 2014

(65) Prior Publication Data
US 2014/0290370 A1 Oct. 2, 2014

Related U.S. Application Data

(60) Provisional application No. 61/786,432, filed on Mar. 15, 2013.

(51) Int. Cl.
| | | |
|---|---|---|
| G01N 29/24 | (2006.01) | |
| G01N 29/036 | (2006.01) | |
| G01N 21/77 | (2006.01) | |
| G02B 6/293 | (2006.01) | |

(52) U.S. Cl.
CPC ...... *G01N 29/2418* (2013.01); *G01N 21/7746* (2013.01); *G01N 29/036* (2013.01); *G01N 2291/014* (2013.01); *G01N 2291/0256* (2013.01); *G02B 6/29338* (2013.01)

(58) Field of Classification Search
CPC ............ G01N 29/2418; G01N 21/7746; G01N 29/036; G01N 2291/0256; G01N 2291/041; G01N 2291/0257; G01N 29/022; G01N 29/42; G01N 2291/0255; G02B 6/29341

USPC ............... 73/643, 655–657, 24.01, 24.02; 250/339–343
See application file for complete search history.

(56) References Cited

U.S. PATENT DOCUMENTS

| | | | | |
|---|---|---|---|---|
| 5,929,430 A | * | 7/1999 | Yao | H01S 5/065 |
| | | | | 250/205 |
| 2006/0019373 A1 | * | 1/2006 | Kahlman | G01N 27/745 |
| | | | | 435/287.2 |
| 2009/0263137 A1 | * | 10/2009 | Hossein-Zadeh | H04B 1/30 |
| | | | | 398/115 |
| 2010/0238454 A1 | * | 9/2010 | Pruessner et al. | 356/479 |
| 2012/0194803 A1 | * | 8/2012 | Song | G01N 21/41 |
| | | | | 356/128 |
| 2012/0320449 A1 | * | 12/2012 | Savchenkov | H01S 5/0687 |
| | | | | 359/340 |
| 2013/0003766 A1 | * | 1/2013 | Savchenkov | G04F 5/14 |
| | | | | 372/38.01 |

(Continued)

OTHER PUBLICATIONS

Mass Sensing with Optomechanical Oscillation, CLEO Technical Digest OSA, 2012.*

(Continued)

*Primary Examiner* — Laura Martin
*Assistant Examiner* — Suman K Nath
(74) *Attorney, Agent, or Firm* — Keith A. Vogt; Vogt IP

(57) ABSTRACT

An optical microresonator based RF oscillator sensor for measuring mass, temperature, and particle/molecule concentration. An optical energy source is coupled to the optical microresonator to generate optical power oscillations at Rf frequencies. A stable or reference RF oscillation frequency is established which allows for measuring oscillation frequency variations induced by the interaction of the substance with the optical microresonator.

16 Claims, 11 Drawing Sheets

(56) References Cited

U.S. PATENT DOCUMENTS

| | | | |
|---|---|---|---|
| 2013/0068025 A1* | 3/2013 | Medin | G01N 29/022 73/579 |
| 2013/0098141 A1* | 4/2013 | McCaig | G01N 5/02 73/24.06 |
| 2014/0110572 A1* | 4/2014 | Li et al. | 250/227.23 |
| 2015/0020590 A1* | 1/2015 | Painter | G01P 15/093 73/514.26 |

OTHER PUBLICATIONS

Mass sensing with optomechanical oscillation, CLEO Technical Digest OSA 2012.*

Deng et al.; Thermo-optomechanical oscillator for sensing applications; , CLEO conference Jun. 2013, JTu4A.37 (Nanophotonics, Lightwave Communications and Biophotonics poster Session); Optical Society of America; US.

Deng et al; Thermo-optomechanical oscillator for sensing applications, Optics Express, vol. 21, No. 4, pp. 4653-4664, Feb. 2013; Optical Society of America, US.

Liu et al.; "Mass Sensing with Optomechanical Oscillation", CLEO conference May 2012, JW2A.110; Optical Society of America; US.

Liu et al.; Mass sensing with optomechanical oscillation, IEEE Sensors, vol. 13, No. 1, pp. 146-147, Jan. 2013; IEEE, US.

Liu et al.; "On the Performance and Sensitivity Limit of Mass Sensing with Optomechanical Oscillation", CLEO conference Jun. 2013, CM4O.8 (Micro-Sensors session); Optical Society of America, US.

Liu et al; "Sub-pg mass sensing and measurement with optomechanical oscillator", Optics Express, vol. 21, No. 17, pp. 19555-19567, Aug. 2013; (Also appeared on Virtual Journal for Biomedical Optics (VJBO), vol. 8(9), Oct. 2013).

* cited by examiner

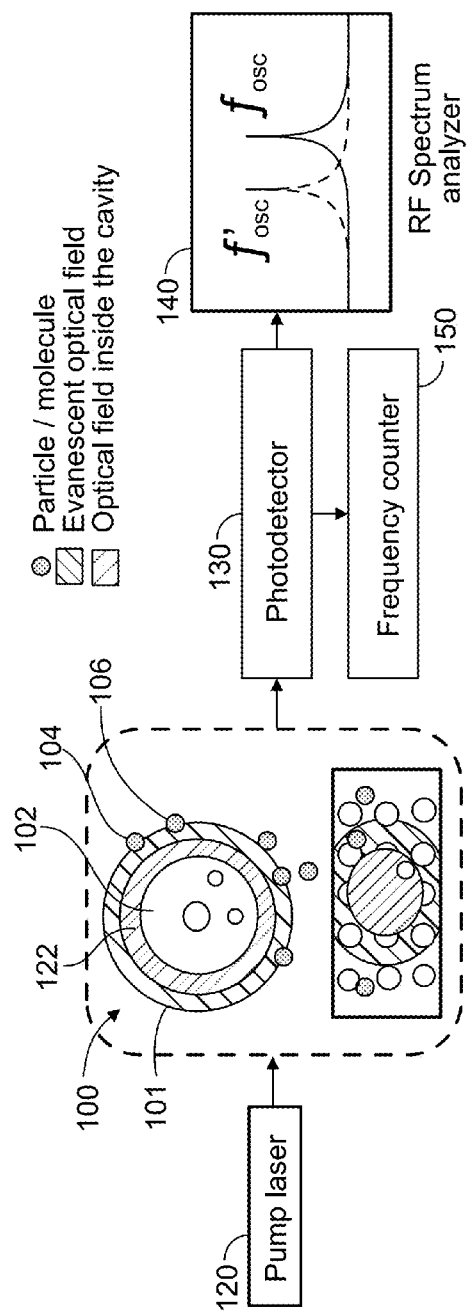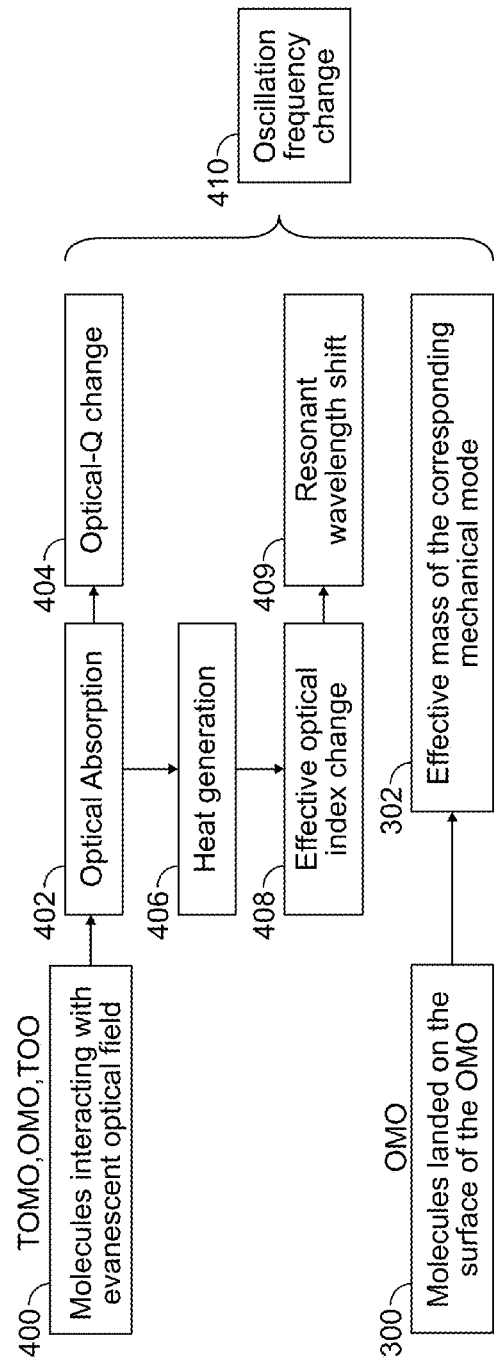
FIG. 1
FIG. 2

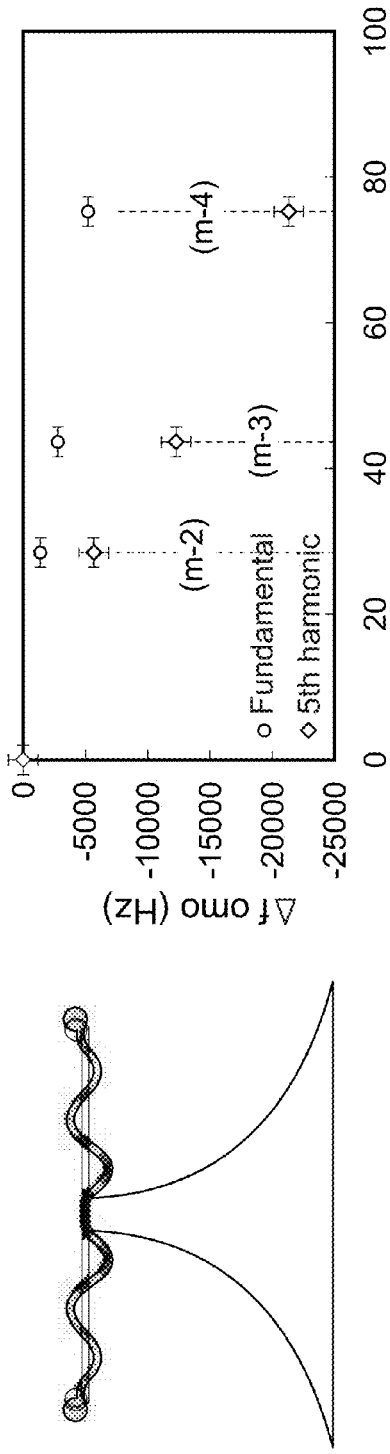
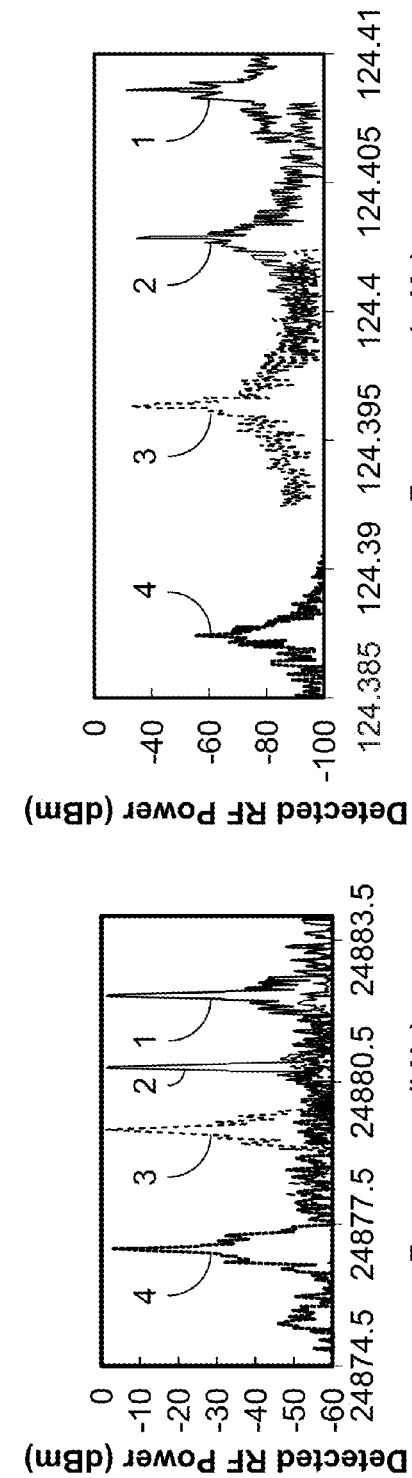
FIG. 10A
FIG. 10B
FIG. 10C
FIG. 10D

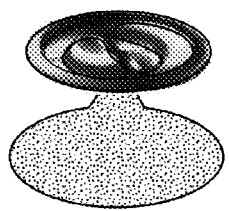 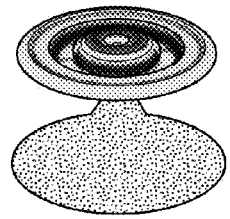 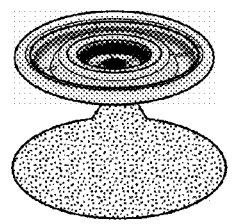
FIG. 11A      FIG. 11B      FIG. 11C
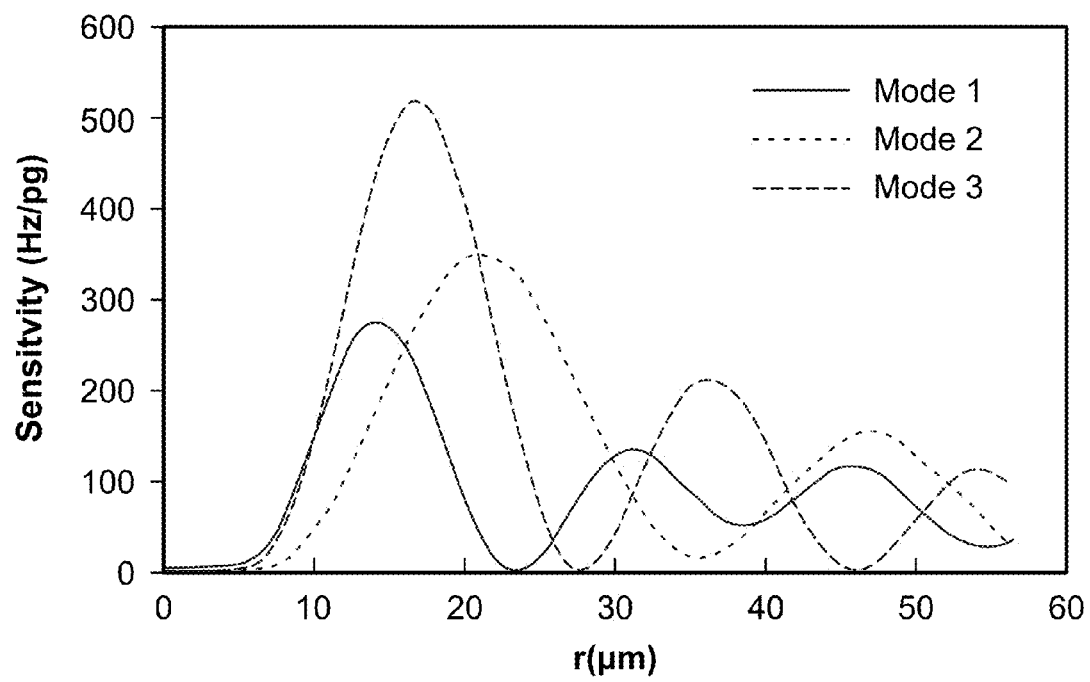
FIG. 11D

SENSORS USING OPTICAL RF OSCILLATORS

CROSS-REFERENCE TO RELATED APPLICATIONS

This application claims the benefit U.S. Provisional Application No. 61/786,432, filed Mar. 15, 2013 and herein incorporated by reference.

STATEMENT REGARDING FEDERALLY SPONSORED RESEARCH OR DEVELOPMENT

This work was supported by AFOSR grant FA9550-12-1-0049 and NSF grant ECCS40559.59.

INCORPORATION-BY-REFERENCE OF MATERIAL SUBMITTED ON A COMPACT DISC

Not Applicable.

BACKGROUND OF THE INVENTION

Field of the Invention

Microresonator based optical and mechanical sensors are devices that can detect and quantify molecules and small particles (micron or nano size) through the sensitivity of their resonant frequency. In resonant optical sensors the interaction between the evanescent optical field and the molecules/particles shifts the resonant frequency (wavelength) of the corresponding optical mode that is directly monitored using temporal or spectral power monitoring. In micro/nano-electromechanical (MEMS and NEMS) sensors the particle molecules that land on the microresonator surface, change the mechanical resonant frequency that is monitored using electronic or optical techniques (mainly non-resonant techniques). The resolution of both resonant optical and mechanical sensors is limited by the linewidth of the corresponding mode. In the case of resonant mechanical sensors external actuation and consequently self-sustained oscillation can be used to increase the oscillation amplitude and decrease the oscillation linewidth.

BRIEF SUMMARY OF THE INVENTION

In one embodiment of the present invention, the sensitivity of the oscillation frequency of Optomechanical (OM), Thermo-optical (TO) or Thermo-Optomechanical (TOM) Oscillators are used as a sensing mechanism to detect and quantify molecules and particles in the vicinity of an evanescent optical field. In addition, the optomechanical oscillator (OMO) may be used for measuring the mass of the molecules/particles that land (are placed) on its surface.

The oscillation frequency of the sensors is affected by changes in the linewidth or resonant wavelength of the corresponding optical mode through interaction of molecules with the evanescent optical field. In addition, for an OM oscillator, molecules may affect the oscillation frequency by changing the effective mass of the mechanical resonator.

The OM oscillator of the present invention also provides a high quality factor (high-Q) guided mode optical resonance (as opposed to free space optical reflection) and optomechanical oscillation (as opposed to electromechanical oscillation) to monitor the mass deposited on a micromechanical resonator. In this approach, the circulating optical power inside a high-Q optical microcavity (that is also a micromechanical resonator) serves as both a sensitive read-out and efficient actuator to generate and monitor optomechanical oscillations.

The OM oscillator of the present invention avoids the general drawbacks of electromechanical sensors by measuring optically induced oscillations of a sensor. This permits use in applications that are unsuitable to electronics. In addition, the present invention achieves high levels of sensitivity. The sensor of the present invention takes advantage of the large circulating optical power inside a high-Q resonator, which, simultaneously serves as an efficient actuating force and sensitive read-out mechanism. The oscillators (OM,TO,TOM) of the invention improve the simplicity and accuracy of the read-out mechanism (as opposed to conventional resonant optical sensors that use optical spectrum or power monitoring) by direct translation of optical resonant shift to RF resonant shift. Moreover the RF signal can be used for remote sensing applications through a wireless link.

BRIEF DESCRIPTION OF THE SEVERAL VIEWS OF THE DRAWINGS

FIG. 1 is a schematic diagram of one embodiment of the present invention.

FIG. 2 is a flow chart illustrating the physical mechanisms used by the present invention.

FIG. 10A is a FEM simulation of the deformation for one the mechanical modes of the microtoroid shown in FIG. 9.

FIG. 10B is a graph of the measured oscillation frequency shift plotted against the loaded mass for the distributions shown in FIGS. 9B-9D for the fundamental ($f_{OMO}$) and fifth harmonic ($5 \times f_{OMO}$) of the mode shown in FIG. 10A.

FIG. 10C shows the detected RF spectrum of the microtoroidal optomechanical oscillator shown in FIG. 9 near the fundamental frequency corresponding to the mode shown in FIG. 10A in the presence of various amounts of loaded mass corresponding to the distributions shown in FIGS. 9B-9D.

FIG. 10D shows the detected RF spectrum of the microtoroidal optomechanical oscillator shown in FIG. 9 near a second eigen frequency corresponding to the mode shown in the insert in the presence of various amounts of loaded mass (corresponding to the distributions shown in FIGS. 9B-9D).

FIGS. 11A-11C are FEM simulations of the deformation for three eigen mechanical modes of the microtoroidal optomechanical oscillator shown in FIG. 9.

FIG. 11D is a graph of the calculated mass sensitivity of the oscillation frequency ($\eta$) for the oscillator modes shown in FIG. 11A-11C plotted against radial position of the mass on a microtoroid having a major diameter of 133 μm and a pillar diameter of 11.3 μm.

DETAILED DESCRIPTION OF THE INVENTION

Figure 3:
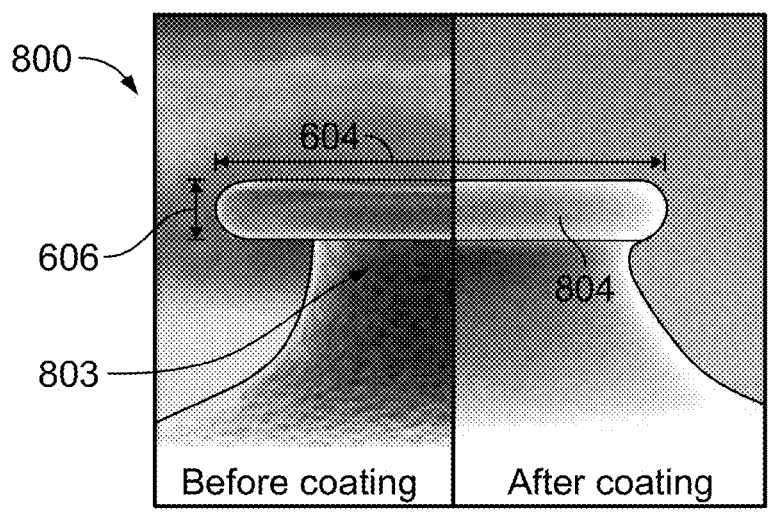
FIG. 3 is a SEM image of the microtoroid before (left half) and after (right half) coating with PMMA.

This description is not to be taken in a limiting sense, but is made merely for the purpose of illustrating the general principles of the invention. The scope of the invention is defined by the appended claims. In a preferred embodiment, the present invention can be implemented using three classes of optical RF oscillators independent of the material system and specific configuration employed in the structure of the oscillator. First, an optomechanical oscillator (OMO) may be used. In an OMO, the interplay between mechanical deformation (due to radiation pressure or gradient optical force of a resonant optical field) and resonant optical power inside a high quality factor (high-Q) optical resonator, results in modulation of the transmitted optical power near one of the mechanical resonant frequencies of the structure.

A stable or reference optomechanical oscillation frequency as well as the exact oscillation frequency is determined by: 1) wavelength detuning which is the wavelength difference between the pump laser and the resonant wavelength. At a fixed pump wavelength, detuning depends on the magnitude of the resonant wavelength and therefore the effective refractive index of the optical mode with the resonant wavelength being proportional to the effective index. 2) loaded quality factor of the corresponding optical mode, 3) the effective mass of the responding mechanical mode, 4) temperature and 5) magnitude of optical input power.

Another oscillator that may be used with the present invention is a thermo-optical oscillator (TOO). Two types of optical microresonators can function as a TOO. The first are high-Q microresonators. Another is hybrid microresonators (such as polymer-coated microresonators) where the optical mode partially resides in two materials with opposite thermo-optical coefficients (i.e $dn_1/dT>0$ and $dn_2/dT<0$).

In yet another embodiment, thermo-optomechanical oscillators (TOMO) may also be used. Two types of optical microresonators can function as a TOMO. The first are microresonators made of materials with a negative thermo-optical coefficient (dn/dT<0) and a relatively large expansion coefficient. Another is hybrid microresonators (such as polymer-coated microresonators) where dn/dT>0 and dR/dT<0 (which happens for certain polymer coated microresonators) then both thermal and mechanical (expansion) effects contribute in the dynamics of the system resulting in thermo-optomechanical oscillation with a characteristic temporal behavior consisting of short and long period oscillations.

The stable oscillation or reference frequency of TOO and TOMO is determined by 1) wavelength detuning which is the wavelength difference between the pump laser and the resonant wavelength. At a fixed laser power detuning depends on the magnitude of the resonant wavelength and therefore the effective refractive index of the optical mode with the resonant wavelength being proportional to the effective index. 2) loaded quality factor of the corresponding optical mode. 3) temperature and 4) magnitude of optical input power.

As shown in FIG. 1, the evanescent optical field 101 of a high-Q optical mode is the field that extends into surrounding medium and interacts with the substance to be detected. Substances to be detected include, but are not limited to, molecules and or particles 104 and 106 residing in the vicinity of the optical microresonator 100 having an upper surface 102 and as a result the resonant wavelength and/or the quality factor (Q-factor) of corresponding optical mode changes. Since the oscillation frequency of an oscillator depends on the resonant wavelength and optical Q-factor of the optical mode involved in the oscillation, changes in molecule concentrations are translated into changes in RF oscillation frequency. While one embodiment of the invention concerns a microtoroid as the oscillator, which has an optical field 122 inside a cavity, other devices such as microdisks, microrings, microspheres, microtoroids or photonic crystals may be used as well. The implementation of these devices with the present invention is within the scope of the invention as well.

Molecules change the effective refractive index and/or the Q-factor of a resonant optical mode through three different mechanisms: 1) Molecule polarization: where the effective index of the corresponding optical mode changes due to electric polarization of the molecules in the evanescent field (the presence of molecules increases the effective index); 2) Thermal effect: where the absorption of the evanescent optical field generates heat and through thermo-optic effect (temperature change) it affects the effective refractive index; and 3) Absorption effect on Q-factor: where the absorption of the optical field by the molecule degrades the quality factor of the resonant optical mode.

In another embodiment, the absorption effect on the Q-factor may be significantly enhanced by choosing an optical pump wavelength close to one of the absorption lines of the target molecule. For example, operating the sensor in Mid-IR regime which is where most gas molecules have a large optical absorption cross-section, can make the oscillation frequency of TOMO, OMO or TOO sensitive to certain molecules through optical quality factor degradation and thermal effects.

In addition to the above mechanisms, when a molecule or particle lands on the surface of an optomechanical oscillator (OMO), the oscillation frequency changes due to changes in the effective mass of corresponding mechanical mode.

In another embodiment, the present invention includes a pump laser with a wavelength $\lambda_p$ coupled to a high-Q optical mode of a microresonator. Above a certain threshold pump power the transmitted optical power is modulated through optomechanical, thermo-optomechanical or thermo-optical interaction. The nature of interaction depends on the microresonator design and structure. The specific interaction and device characteristics determine the modulation frequency (frequencies).

In a preferred embodiment of the invention, optical microresonator based RF oscillators may be used as sensors. Coupling an optical energy source 120 to an optical microresonator generates optical power oscillations. A stable or reference oscillation frequency is established which allows for measuring the oscillation frequency variations induced by a substance to be measured 104 and 106 as the substance interacts with optical microresonator 102. Oscillation frequencies are then monitored by converting optical power oscillations into electronic signals by a photodetector 130. In turn, an RF spectrum analyzer 140 or a frequency counter 150 measures the electronic signals. In addition, both an RF spectrum analyzer 140 and frequency counter 150 may be used together.

In another preferred embodiment of the invention, optical microresonator based RF oscillators may be used as mass sensors by using radiation pressure driven optomechanical RF oscillators. Optical power oscillations are generated by coupling an optical energy source 120 to optomechanical microresonator 102 and establishing a stable or reference oscillation frequency. Changes in oscillation frequency variation induced by added mass on the optomechanical microresonator are then measured. The oscillation frequency may also include a fundamental frequency and harmonic frequencies. The harmonic frequencies may also be used to measure the variations induced by added mass on the optomechanical microresonator with improved sensitivity. The oscillation frequency may be monitored by converting optical power oscillations into electronic signals by a photodetector 130. In turn, the electronic signals are measured by an RF spectrum analyzer 140 or a frequency counter 150. In addition, both an RF spectrum analyzer 140 and frequency counter 150 may be used together.

In another preferred embodiment of the invention, optical microresonator based RF oscillators may be used as molecule concentration sensors by generating, optical power oscillations by the coupling of an optical energy source 120 to the optical microresonator 102. A stable or reference oscillation frequency is established and the oscillation frequency variations induced by the molecules to be sensed or measured are measured as the molecules interact with the evanescent optical field 100 of optical microresonator 102.

The oscillation frequency may be monitored by converting optical power oscillations into electronic signals by a photodetector 130. In turn, the electronic signals are measured by an RF spectrum analyzer 140 or a frequency counter 150. In addition, both an RF spectrum analyzer 140 and frequency counter ISO may be used together.

OMO, TOO, and TOMO oscillators may be used as concentration sensors. In addition, optoelectronic oscillators may be used as concentration sensors as well.

FIG. 2 shows the interaction mechanisms of the sensors for the various configurations of optical microresonators described above. For molecules that interact with the surface of an OMO 300 the effective mass of the device is altered 302 creating a change in oscillation frequency 410 which may be measured as described above.

In applications in which a substance or molecule interacts with the evanescent field 400 optical absorption occurs 402 which creates an optical-Q change 404. This creates a change in oscillation frequency 410 which may be measured as described above.

Optical absorption 402 may also result in heat generation 406 that changes the effective optical index 408 resulting in a resonant wavelength shift 409. This creates a change in oscillation frequency 410 which may be measured as described above.

Molecules interacting with the evanescent field 400 also change the effective optical index 408 resulting in a resonant wavelength shift 409. This creates a change in oscillation frequency 410 which may be measured as described above.

In another embodiment, the present invention measures the resonant optical wavelength shift resulting from the interaction of molecules with the evanescent optical field of the sensor. Conventionally the wavelength shift and the quality factor changes in the sensor may be measured based on temporal or spectral variations of the optical power. By using different types of optical oscillators (i.e TOMO, TOO, and TOMO), the wavelength shift is directly translated to an RF frequency shift that may be measured, and which may also be transmitted wirelessly for remote sensing. Moreover, measuring small optical power variations is a difficult task due to the small signal-to-noise ratio. In contrast, the oscillation frequency of a narrow linewidth optically driven RF oscillator can be tracked with relatively large signal-to-noise ratio. Filially passive optical microresonators are not sensitive to added mass while OMO sensors can also detect mass of one or more molecules and other objects.

In another embodiment of the invention as shown in FIG. 3, a self-sustained thermo-optomechanical oscillator based on a PMMA coated silica microtoroid is provided. The thick PMMA coating modifies the thermo-mechanical and thermo-optical effects resulting in a hi-frequency oscillation. The hi-frequency oscillation consists of fast/high and slow/low periods enabling independent monitoring of local (near the optical mode) and global effects. At a fixed laser wavelength close to the resonant wavelength or stable frequency of the microresonator, self-sustained temporal oscillation ensues and the transmitted optical power is modulated by a unique waveform that consists of fast and slow oscillation periods.

Figure 4A:
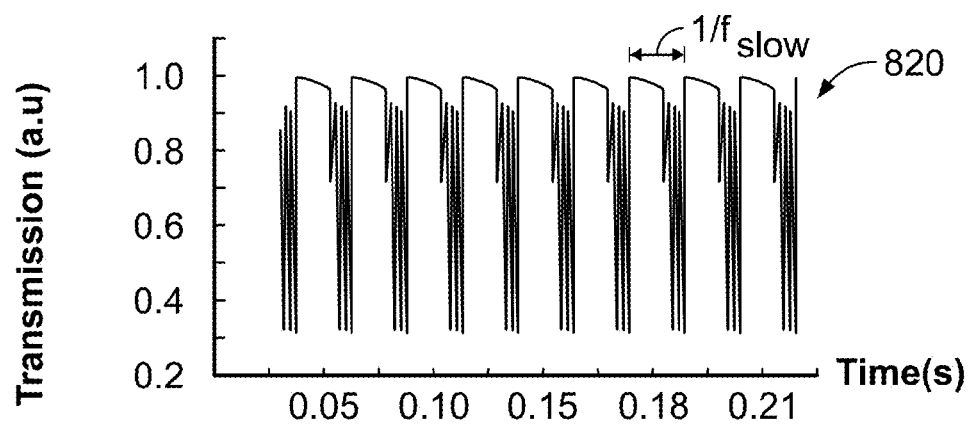
FIG. 4A is a graph showing the slow/low and fast/high bi-frequency cycles of one embodiment of the present invention with temporal variations of the modulated transmitted optical power through the fiber-taper that is coupled to the hybrid microtoroid (FIG. 3) at a fixed laser wavelength.
Figure 4B:
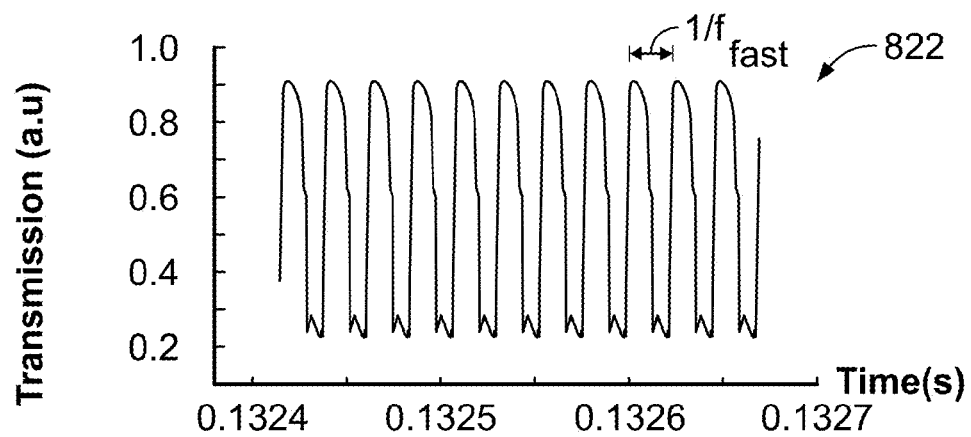
FIG. 4B is an enlarged view of the fast/high oscillation cycles.
Figure 5:
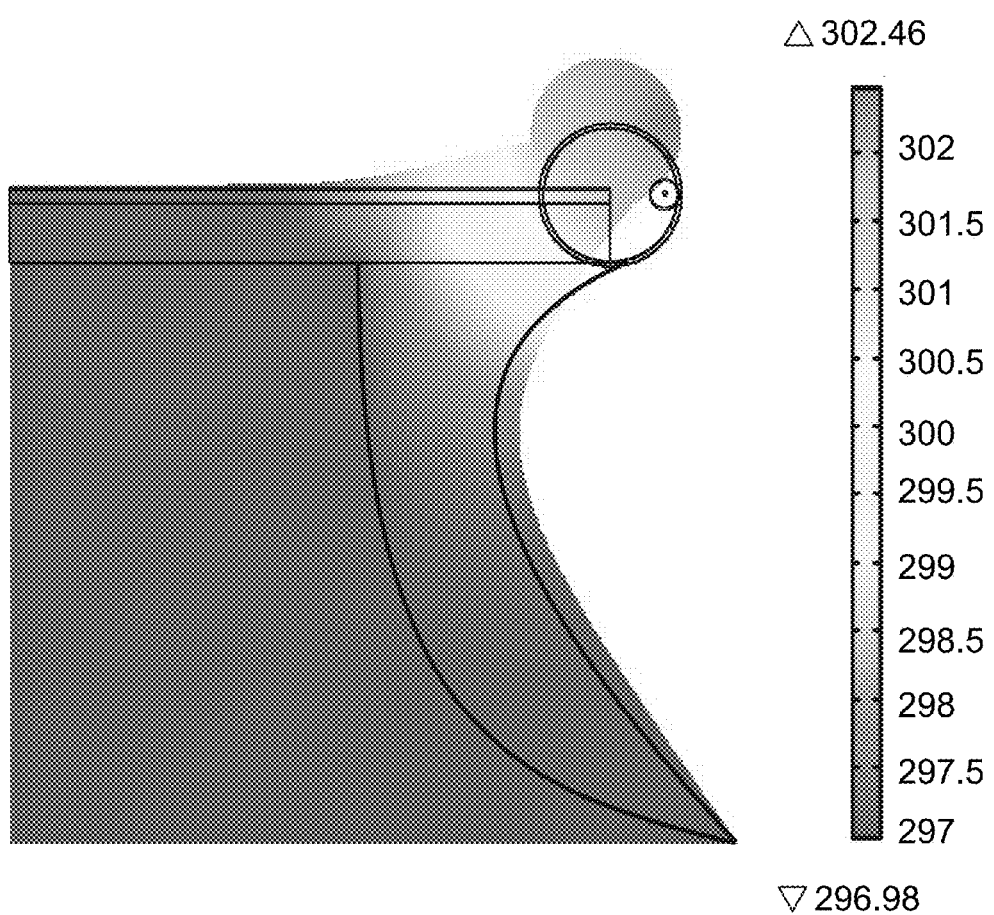
FIG. 5 is a finite element modeling (FEM) of the thermally induced deformation caused by expansion of residual PMMA underneath the toroidal structure shown in FIG. 3.

As shown in FIG. 4, the oscillation consists of a slow oscillation 820 with a frequency of $f_L$ in the 10-300 Hz range and a fast oscillation 822 with a frequency of $f_H$ in the 10-100 kHz range. The slow oscillation is generated by the wavelength shift induced by thermo-mechanical deformation of the bimorph structure as shown in FIG. 5. The fast oscillation is generated by the wavelength shift due to thermo-optic effect in silica and PMMA. An application for the oscillator may be used as a sensor to measure the sensitivity of oscillation frequencies as a result of changes in humidity.

In one embodiment, the thermo-optomechanical oscillator 800 is a silica microtoroid cavity coated by a 200 nm thick PMMA layer as shown in FIG. 3. Half of the microtoroid is uncoated 803 and section 804 is coated with PMMA resulting in a major diameter of 42 μm 604 and a minor diameter 606 of 5.5 μm. Prior to coating, the microtoroid had an intrinsic quality factor ($Q_{int}$) of the $3.2 \times 10^7$. After PMMA coating, the $Q_{int}$ dropped to $2.3 \times 10^6$ due to the absorption loss in PMMA.

Line 820 of the graph shown in FIG. 4 measured the detected transmitted optical power through the fiber-taper coupled to the hybrid microtoroid 800 at a fixed laser wavelength detuned by 62 pm from WGM resonant wavelength. The optical input power was 2.14 mW. Line 822 shows the fast oscillation cycles.

FIG. 5 is a FEM modeling of the thermally induced deformation caused by expansion of residual PMMA underneath the toroidal structure. The input optical power is 1 mW resulting in a circulating optical power of ~3 W.

Figure 6A:
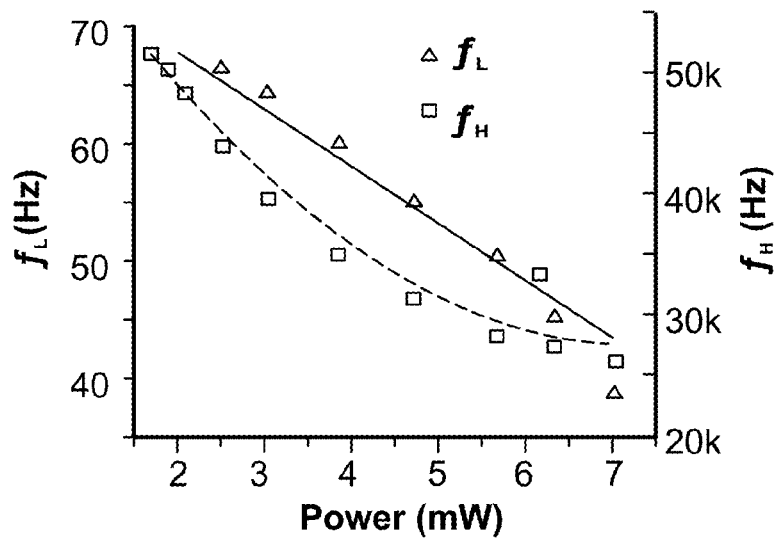
FIG. 6A is a graph of the high/fast and low/slow thermo-optomechanical oscillation frequencies plotted against optical input power.
Figure 6B:
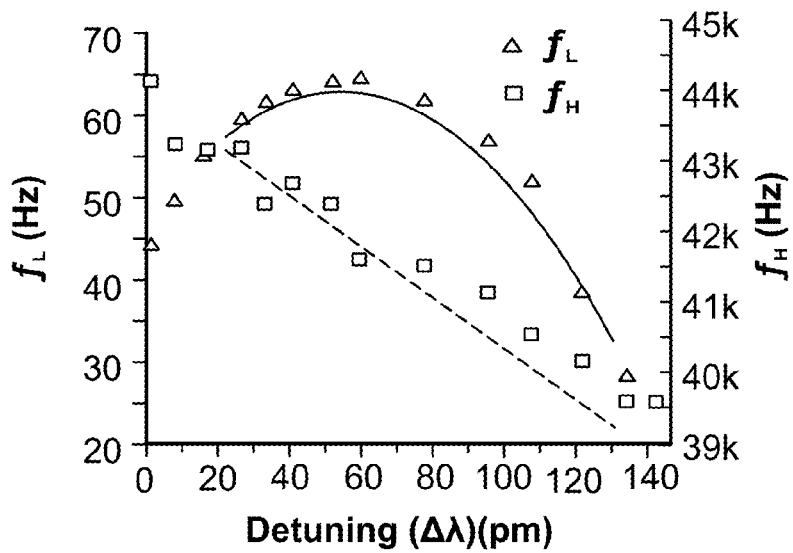
FIG. 6B is a graph of the fast and slow thermo-optomechanical oscillation frequencies plotted against wavelength detuning.
Figure 6C:
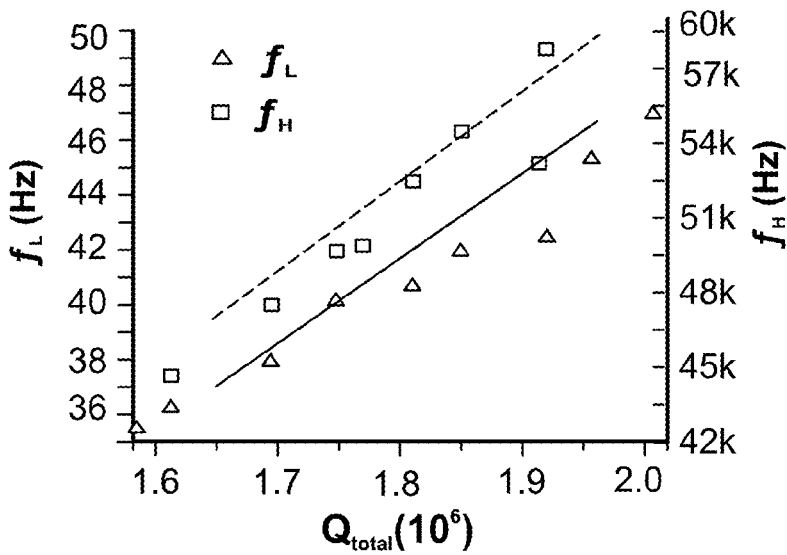
FIG. 6C is a graph of the fast and slow thermo-optomechanical oscillation frequencies plotted against total optical-Q.

As shown in FIGS. 6A-6C, the magnitude of ($f_L$ and $f_H$) are strongly dependent on input power, loaded quality factor and wavelength detailing. The sensitivity of the TOMO to wavelength detuning and quality factor makes the device suitable for use as a sensor.

Figure 7A:
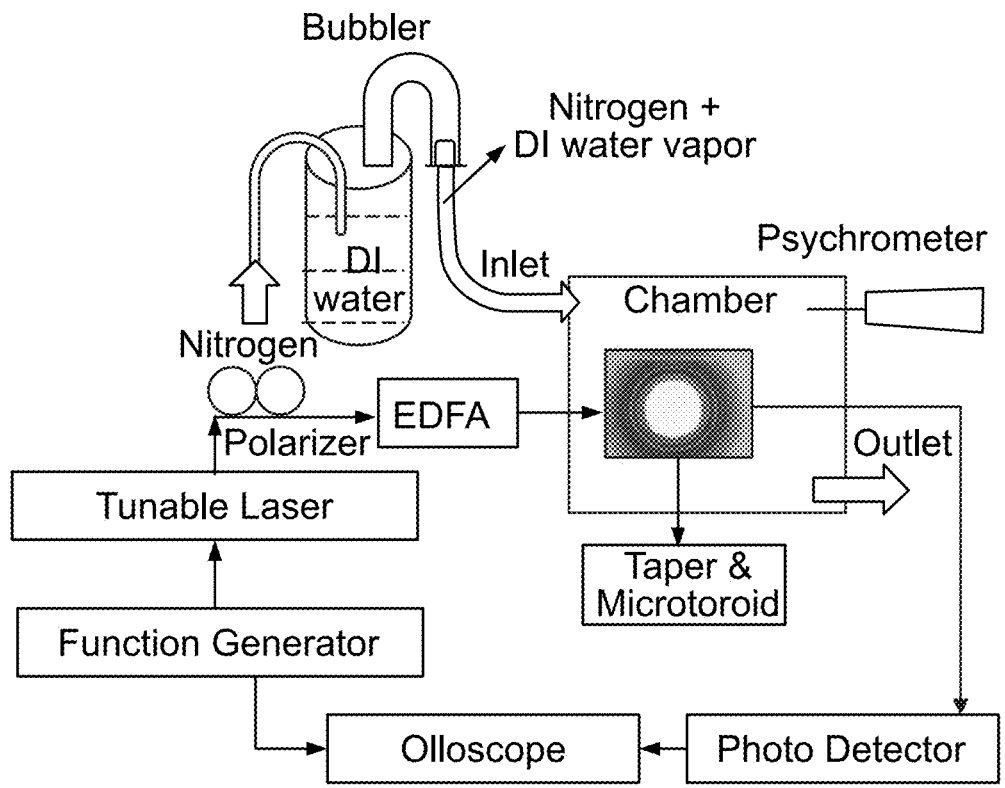
FIG. 7A shows a configuration that may be used for humidity sensing.

An advantage of the invention is that the quality factor and resonant wavelength variations are directly translated to the frequency domain eliminating the need for a tunable laser for spectral monitoring. FIG. 7A shows a configuration that may be used for humidity sensing.

Figure 7B:
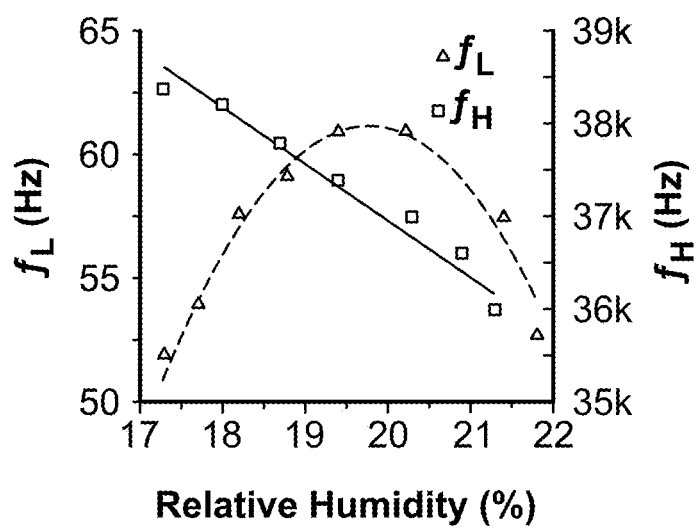
FIG. 7B is a graph of the measured fast and slow thermo-optical oscillation frequencies plotted against relative humidity.

FIG. 7B shows the measured values of $f_L$ and $f_H$ in the detected waveform plotted against relative humidity (RH) while all other parameters are kept constant. The combination of the parabolic behavior of $f_L$–RH and the linear behavior of $f_H$–RH serves as a powerful read-out mechanism for gas sensing. $f_H$ and $f_L$ individually can be used for measuring changes in RH while the $f_H$–$f_L$ crossing points provide references for measuring absolute RH values. Assuming a frequency resolution of 10 Hz the slope of $f_H$–RH (611 Hz/RHU) corresponds to a minimum detectable RH change of 0.016%. Calculations show the contribution of wavelength shift and Q-variation (absorption) are 424 Hz/RHU and 187 Hz/RHU respectively (RHU≡1% RH).

Figure 8A:
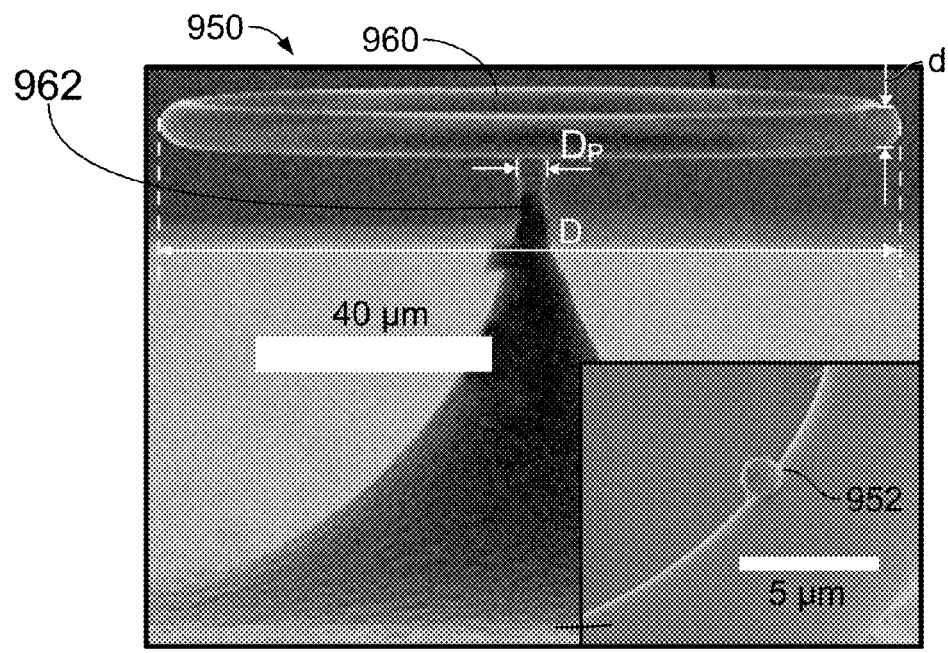
FIG. 8A is a SEM image of an embodiment showing the silica microtoroid under test with an insert showing a close-up view of the particle landed on the toroidal section (m~1.6 pg).
Figure 8B:
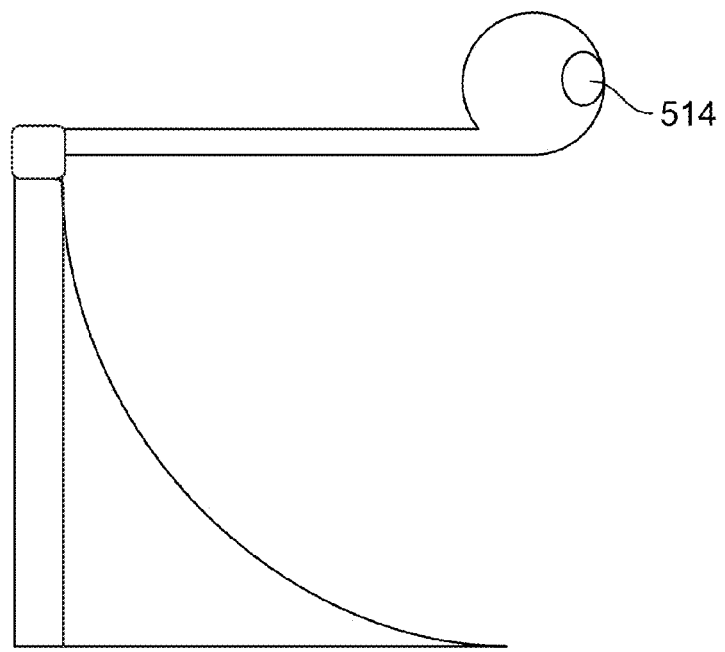
FIG. 8B shows the optical mode of one embodiment of the invention.

In one preferred embodiment wherein the oscillator functions as a mass sensor, a high-Q microtoroid 950 is provided as shown in FIG. 8A. Microtoroid 950 is a well-known optical microcavity that consists of a silica microtoroid 960 as shown on top of a silicon pillar 962 as shown in FIG. 8A. The device also has an optical mode 514 as shown in FIG. 8B.

The toroidal region of the silica microtoroid supports high-Q optical Whispering-Gallery (WG) modes ($Q_0 > 10^7$, $Q_0 = \lambda_{res}/\delta\lambda$: intrinsic optical quality factor). The microdisk membrane supports high-Q mechanical modes with mechanical quality factors ($Q_{mech}$) in excess of 1000.

Microdisk vibration modulates the resonant wavelength of the optical WG modes circulating inside the toroid and consequently the transmitted optical power. Due to narrow optical linewidth ($\delta\lambda$) of WG modes, sub-picometer radial displacement can generate detectable optical intensity modulation.

When the optical input power ($P_{in}$) is above the optomechanical oscillation threshold power ($P_{th}$), the radiation pressure, of the circulating optical power combined with the optical path length modulation results in self-sustained optomechanical oscillation at the corresponding mechanical eigen frequency ($f_{OMO}$).

At low optical input power levels, the linewidth of the mechanical modes are thermally excited and therefore the passive resonant linewidth in the RF spectrum (that is determined by $Q_{mech}$) limits the resolution of the frequency measurement. Above threshold ($P_{in} > P_{th}$) the optomechanical gain narrows down the oscillation linewidth to sub-Hz regime and enables ultra-high resolution detection of frequency variations.

As described above, the optical power of a tunable laser is coupled to the optical cavity through silica fiber-taper and the spectrum of the amplitude variation of transmitted optical power is monitored with an RF spectrum analyzer upon detection in a photodetector.

The resulting sensor optomechanical oscillator (OMO) of the present invention functions as a high sensitivity mass sensor where the mechanical resonator, high-Q optical readout, and optical actuation are all combined in a single device. A laser provides the optical power for actuation and high resolution monitoring of the mechanical resonant frequency through ultra-narrow linewidth optomechanical oscillation. Mass sensing with sub-picogram resolution using a silica microtoroid OMO is obtained while the total power consumption of this device is below 1 mW.

In yet another embodiment, as shown in FIG. 8, microtoroid OMO 950 may be used to measure the mass of polyethylene microsphere 952. As shown in FIGS. 10A-10D, $f_{OMO}$ shifts proportional to the total external mass added.

Figure 9A:
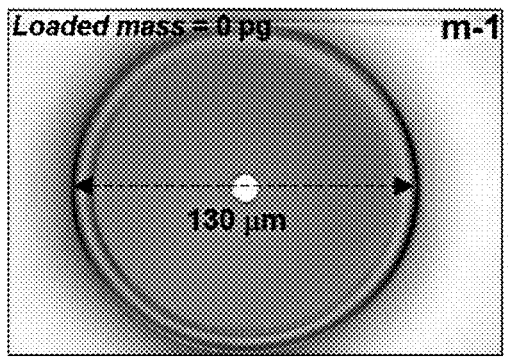
FIG. 9A is a top view micrograph of one microtoroidal OMO of the present invention.
Figure 9B:
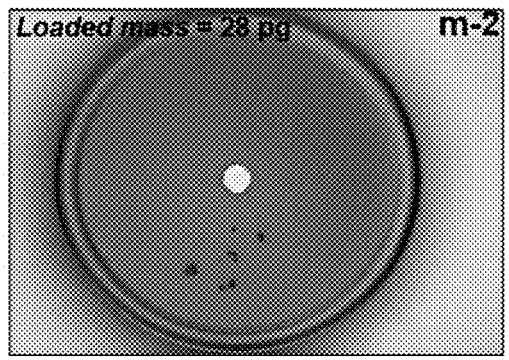
FIGS. 9B-9D are top view micrographs of one OMO of the present invention loaded with polyethylene microspheres.
Figure 9C:
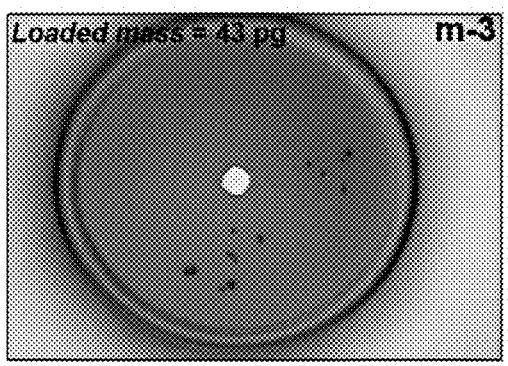
Figure 9D:
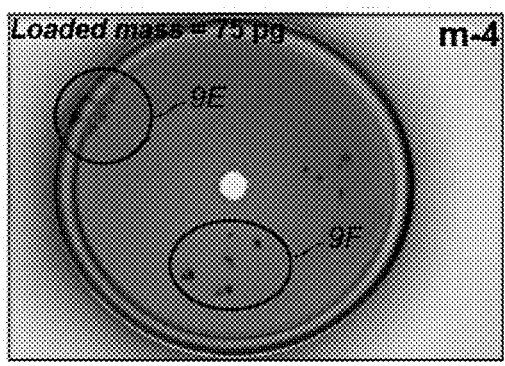
Figure 9E:
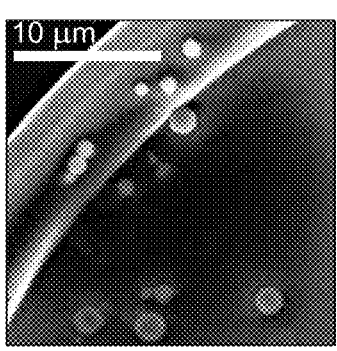
FIG. 9E is an exploded view of the portion indicated as 9E in FIG. 9D.
Figure 9F:
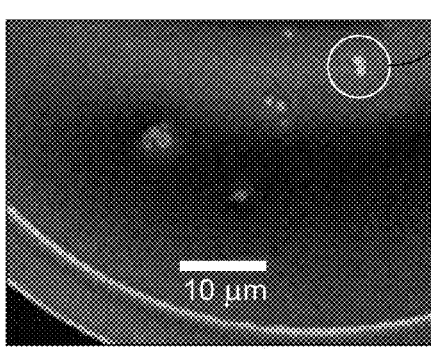
FIG. 9F is an exploded view of the portion indicated as 9D in FIG. 9D.
Figure 9G:
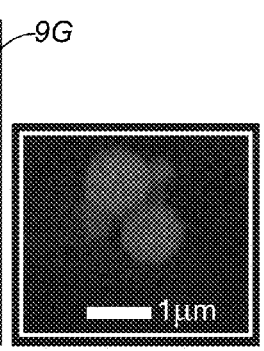
FIG. 9G is an exploded view of the portion indicated as 9G in FIG. 9F.

FIGS. 8 and 9A-9G show OMOs loaded with various masses. In FIG. 9A, the mass is zero. In FIG. 9B, the loaded mass of the polyethylene microspheres is 28 pg. In FIG. 9C, the loaded mass of the polyethylene microspheres is 43 pg. In FIG. 9D, the loaded mass of the polyethylene microspheres is 75 pg. The microspheres were loaded using a piezo-controlled tip on a microtoroid having a major diameter of 133 μm, minor diameter of 11.2 μm and a Si pillar size of 17.2 μm. The measured loaded optical-Q is $2.3 \times 10^6$. The mechanical mode is symmetric as shown in FIG. 10-A with $f_{OMO}$=24.88 MHz and $Q_{mech} \approx 1466$. The smallest polyethylene microspheres have a mass of 0.1 pg (D=0.5 μm) and the largest was 4 pg (D=2 μm).

The additional mass reduces the $f_{OMO}$. FIG. 10B shows the measured and simulated oscillation frequency shift ($\Delta f_{OMO}$) for different mass distributions shown in FIGS. 9A-9D. $\Delta f_{OMO}$ is a function of particle distribution but the average sensitivity ($\Delta f_{OMO}/\Delta m$) is about 72 Hz/pg.

The sensitivity of the device may be improved using higher order OMO harmonics ($m \times f_{OMO}$) that improve the sensitivity of slope η ($=\Delta_{OMO}/\Delta m$, where $\Delta f_{OMO}$ is the frequency shift induced, by mass Δm). As shown in FIGS. 10B-D, the sensitivity of the OMO in FIG. 9 can be improved by a factor of 5 if the 5th harmonic is measured instead of the fundamental frequency. This results in recorded value of 334 Hz/pg for η.

The OMO can operate based on different mechanical modes of the microtoroidal structure. As such self-sustained oscillation of each one of these modes can be used for mass sensing. FIGS. 11A-C shows the mechanical deformation associated with three different mechanical modes of the microtoroid shown in FIG. 9 calculated using finite element modeling (FEM).

The mass sensitivity of each oscillating mechanical mode is different for different locations of the added mass. FIG. 11D shows the estimated sensitivity (η) for the modes shown in FIGS. 11A-C plotted against radial position of added mass.

Figure 12:
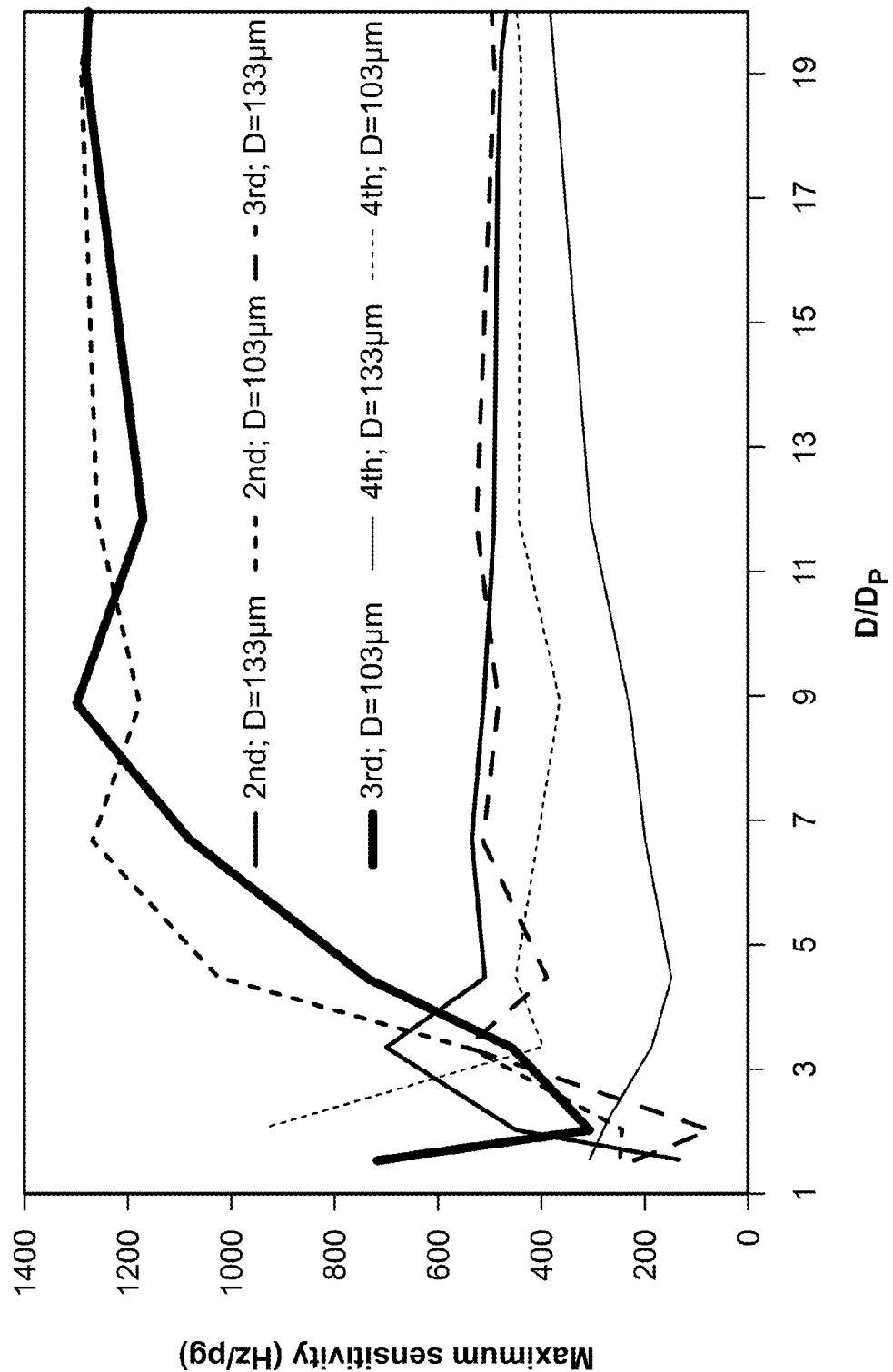
FIG. 12 is a graph of the maximum mass sensitivity ($\eta_{max}$) plotted against $D/D_p$ (ratio between the major diameter of the microtoroid and its pillar diameter) for second, third and fourth modes of microtoroidal OMOs with diameters (D) of 133 and 103 micrometers.

The mass sensitivity of each mechanical mode of a mict\rotoridal OMO with a given major diameter (D) can be optimized by adjusting the pillar diameter ($D_p$). FIG. 12 shows calculated maximum sensitivity ($\eta_{max}$) plotted against $D/D_r$ (the ratio of the microtoroid major diameter and the pillar diameter) for two different values of D and three mechanical modes shown in FIGS. 11A-C.

Figure 13:
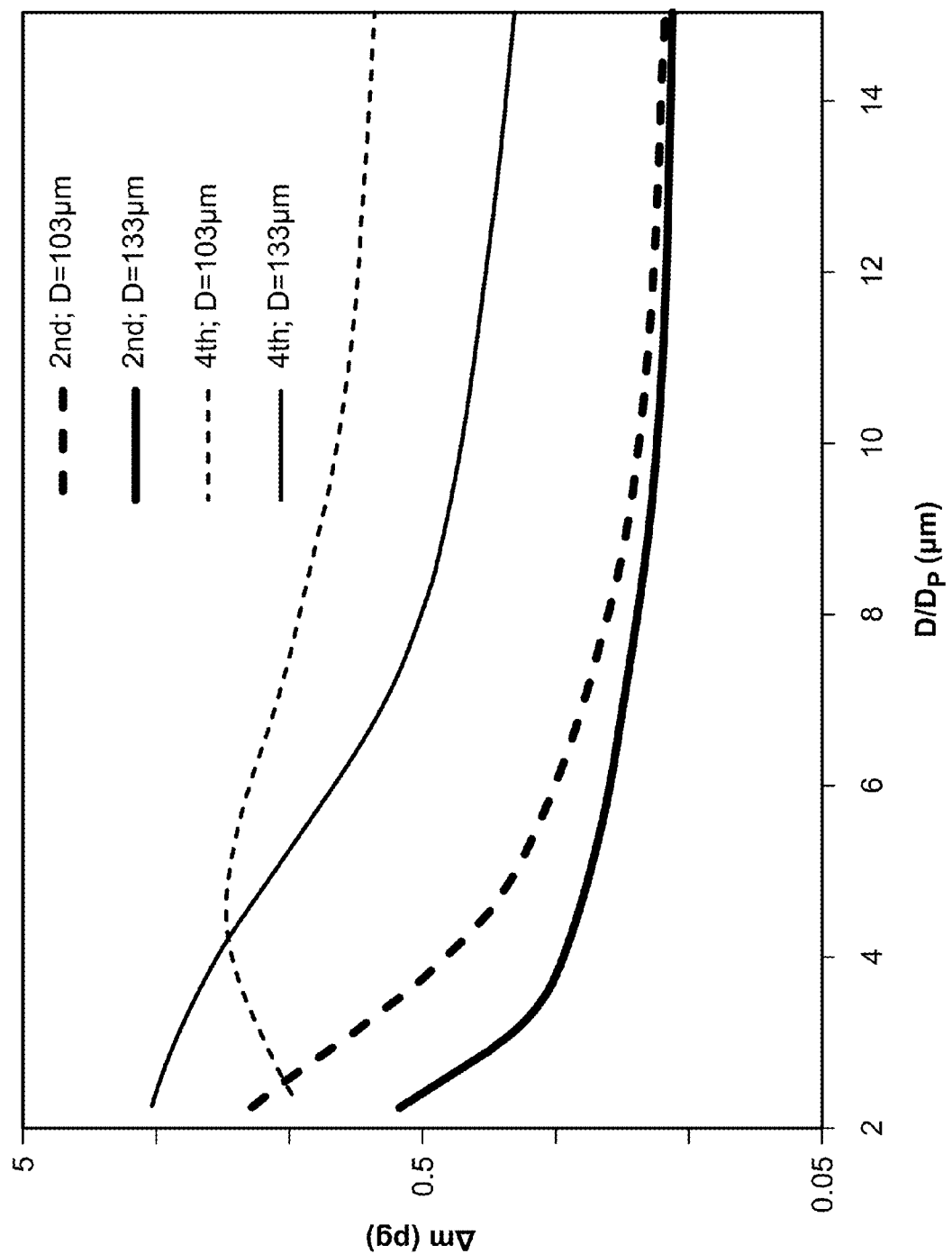
FIG. 13 is a graph of the minimum detectable mass plotted against $D/D_p$ for second and fourth modes of the microtoroidal OMOs with diameters of 133 and 103 micrometers.

The sensitivity of an OMO mass sensor is impacted by laser RIN, wavelength detuning and coupling factor uncertainties on the amplitude oscillation frequency fluctuations ($\delta f_{OMO}$). These parameters contribute to $\delta f_{OMO}$ through optical spring and thermal effects. FIG. 13 shows the minimum detectable mass plotted against $D/D_p$ (the ratio of the microtoroid major diameter and the pillar diameter) based on fifth harmonic shift for D=103 µm (dashed lines) and D=133 µm (solid lines).

What is claimed is:

1. A method of using an optical microresonator based RF oscillator as a sensor comprising the following steps:
    generating optical power oscillations at RF frequencies by coupling an optical energy source to said optical microresonator;
    establishing a stable RF oscillation frequency; and
    optionally measuring the RF oscillation frequency variation induced by a substance to be measured as said substance interacts with said optical microresonator.

2. The method of claim 1 wherein said RF oscillation frequency is monitored by converting optical power oscillations to an electronic signal by a photodetector.

3. The method of claim 2 wherein said electronic signal is measured by a frequency counter.

4. The method of claim 2 wherein said electronic signal is measured by an RF spectrum analyzer.

5. The method of claim 2 wherein said electronic signal is measured by an RF spectrum analyzer and a frequency counter.

6. The method of claim 1 wherein said optical microresonator is an optomechanical oscillator.

7. The method of claim 1 wherein said optical microresonator is a thermo-optical oscillator.

8. The method of claim 1 wherein said optical microresonator is a thermo-optomechanical oscillator.

9. The method of claim 1 wherein said optical microresonator is an optoelectronic oscillator.

10. A method of using a radiation pressure driven optomechanical RF oscillator as a mass sensor comprising the following steps:
    generating optical RF power oscillations by coupling an optical energy source to said optomechanical microresonator, said oscillations are created by said radiation pressure;
    establishing a stable RF oscillation frequency; and
    optically measuring the RF oscillation frequency variation induced by added mass on the optomechanical microresonator.

11. The method of claim 10 wherein said RF oscillation frequency includes a fundamental frequency and harmonic frequencies.

12. The method of claim 11 wherein said harmonic frequencies are used to measure the variation induced by added mass on the optomechanical microresonator.

13. The method of claim 10 wherein an electronic signal is measured by a frequency counter.

14. The method of claim 10 wherein an electronic signal is measured by an RF spectrum analyzer.

15. The method of claim 10 wherein an electronic signal is measured by an RF spectrum analyzer and a frequency counter.

16. A method of using an optical microresonator based RF oscillator having an evanescent field as a molecule concentration sensor comprising the following steps:
    generating optical power oscillations at RF frequencies by coupling an optical energy source to said optical microresonator;
    establishing a stable RF oscillation frequency; and
    optically measuring the RF oscillation frequency variation induced by the molecules to be measured as said molecules interact with said evanescent field of said optical microresonator.

* * * * *